United States Patent [19]
Ueno et al.

[11] Patent Number: 6,139,151
[45] Date of Patent: *Oct. 31, 2000

[54] OPTICAL MEMBER, OBSERVATION APPARATUS WITH THE OPTICAL MEMBER, AND EXAMINATION APPARATUS WITH THE OPTICAL MEMBER

[75] Inventors: Tokio Ueno, Nagoya; Manabu Ota, Gamagori, both of Japan

[73] Assignee: Nidek Co., Ltd., Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/405,841

[22] Filed: Sep. 27, 1999

[30] Foreign Application Priority Data

Sep. 28, 1998 [JP] Japan ................... 10-272926

[51] Int. Cl.⁷ ............................................. A61B 3/10
[52] U.S. Cl. ............................................. 351/220
[58] Field of Search ................... 351/205, 220, 351/221, 232, 233, 215; 358/505, 512, 520, 515; 359/114, 583, 577, 587, 639, 900

[56] References Cited

U.S. PATENT DOCUMENTS

| | | |
|---|---|---|
| 5,629,748 | 5/1997 | Hayashi et al. ................... 351/232 |
| 5,742,374 | 4/1998 | Nanjo et al. . |
| 5,844,659 | 12/1998 | Isogai . |
| 5,886,823 | 3/1999 | Sugano . |
| 5,894,357 | 4/1999 | Murakami ................... 358/515 |
| 5,999,320 | 12/1999 | Shirasaki ................... 359/577 |

FOREIGN PATENT DOCUMENTS

| | | |
|---|---|---|
| 8-52113 | 2/1996 | Japan . |
| 8-122633 | 5/1996 | Japan . |
| 9-304728 | 11/1997 | Japan . |

*Primary Examiner*—George Manuel
*Attorney, Agent, or Firm*—Finnegan, Henderson, Farabow, Garrett & Dunner, L.L.P.

[57] ABSTRACT

Disclosed is an optical member for splitting or combining luminous flux, the optical member including a base body made of a transparent material originally having an internal transmittance of approximately 100%. The base body includes a colored portion which is formed in an entire interior of the base body or on at least one of a light entrance plane and a light exit plane of the base body, whereby the internal transmittance of the optical member is reduced when the luminous flux to be used for observation and examination is split or combined by the optical member. Accordingly, the optical member can reduce the generation of ghost images caused by reflection of the luminous flux by a back plane of the optical member. Also disclosed are an observation apparatus and an examination apparatus for observing or examining an object by means of the luminous flux split or combined by the above optical member.

21 Claims, 6 Drawing Sheets

OPTICAL MEMBER, OBSERVATION APPARATUS WITH THE OPTICAL MEMBER, AND EXAMINATION APPARATUS WITH THE OPTICAL MEMBER

BACKGROUND OF THE INVENTION

1. Field of the Invention

The present invention relates to an optical member for splitting or combining luminous flux to be used for observation, examination, or the like, and an observation apparatus provided with the optical member, and an examination apparatus provided with the same.

2. Description of Related Art

Many observation apparatus and examination apparatus, each of which is provided with a light delivery optical system for delivering luminous flux reflected by an object to the eyes of an observer or an imaging (photographing) unit such as a camera, utilize an optical member such as a semi-transparent mirror for splitting or combining the luminous flux.

For instance, in an ophthalmologic field, there has been known a space-saving type of examination apparatus for examining visual functions of an eye of an examinee (see Japanese patent application laid-open publication No. Hei 8-52113 and counterpart U.S. Pat. No. 5,629,748), which is provided with a beam-splitter shaped like a flat-plate disposed between an optotype disc plate and a concave mirror. In this examination apparatus, a light of an optotype is transmitted through the beam splitter and is reflected by the concave mirror toward the beam splitter. The light is then reflected by a half mirror plane of the beam splitter toward the examinee's eye. Such the beam splitter is usually configured of a base body made of a transparent material, such as glass, originally having the internal transmittance of approximately 100% to visible light, in order to reduce the loss of light caused when the light is transmitted through the beam splitter.

Meanwhile, in a configuration that the flat-plate-like beam splitter is obliquely disposed in an optical path of the optical system, a part of the luminous flux split by the half mirror plane is reflected by a back plane of the beam splitter opposite to the half mirror plane, which causes flares and ghost images. Specifically, luminous flux of the optotype which enters the beam splitter is split into main luminous flux which passes through the half mirror plane and first satellite (ghost) luminous flux which is reflected by the back plane. When the main luminous flux is reflected by the concave mirror and returned to the beam splitter, it is split into regular luminous flux which is reflected by the half mirror plane to be directed to the examinee's eye and second satellite (ghost) luminous flux which is transmitted through the half mirror plane. Thus, the examinee can view an image of the optotype, produced by the regular luminous flux. On the other hand, the first and second satellite (ghost) luminous flux which are split from the main luminous flux and the regular luminous flux at the half mirror plane are both reflected by the back plane to form respective optical paths. As a result thereof, the examinee also will view ghost images produced by the satellite luminous flux.

In the optical apparatus provided with the semi-transparent mirror obliquely disposed in the optical path of the light delivery optical system, flares and ghost images are generated as mentioned above. For measures to prevent the generation of the ghost images which may exert an influence on the regular luminous flux, conventionally, the transmittance and the reflectance of the half mirror plane are so designed as to have the most suitable relation therebetween, or the reflectance of an antireflective film applied on the back plane opposite to the half mirror plane is reduced.

However, a manner of designing the transmittance and the reflectance of the half mirror plane with the most suitable relation therebetween has a spec constraint on apparatus configuration. There is also a limitation in the degree of reduction of the reflectance of the film applied on the back plane of the semi-transparent mirror. Accordingly, the above measures are insufficient to reduce the ghost light to an extent that the ghost light does not become a problem.

If the light amount of ghost light is a problem, it is conceivable to lower the light amount itself of luminous flux which enters the semi-transparent mirror. However, the visual function examination apparatus has a fixed minimum light amount of the optotype image, needed for examination, and therefore only lowering the light amount has its limit. In other apparatus, it is naturally desirable to reduce only the light amount of the ghost light while retaining the light amount of the light beam needed for examination or observation.

SUMMARY OF THE INVENTION

The present invention has been made in view of the above circumstances and has an object to overcome the above problems and to provide an optical member capable of efficiently reducing the influence of ghost light which generates when luminous flux is split or combined through the optical member, an observation apparatus with the optical member, and an examination apparatus with same.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an optical member for splitting or combining luminous flux, the optical member including a base body made of a transparent material originally having an internal transmittance of approximately 100%, the base body having a light entrance plane and a light exit plane and including a colored portion whereby an internal transmittance of the optical member is reduced.

According to another aspect of the present invention, there is provided an observation apparatus for observing or imaging an object by means of observation luminous flux which is a light reflected from or transmitted through the object illuminated, the apparatus including an illumination light source for emitting an illumination light to illuminate the object, a light delivery optical system for delivering the observation luminous flux from the object illuminated by the illumination light source to an eye of an observer or an imaging unit, and an optical member for splitting or combining the observation luminous flux, the optical member being disposed obliquely in an optical path of the light delivery optical system, and the optical member including a base body made of a transparent material originally having an internal transmittance of approximately 100%, and the base body having a light entrance plane and a light exit plane and including a colored portion whereby an internal transmittance of the optical member is reduced.

Furthermore, according to another aspect of the present invention, there is provided an examination apparatus for examining or measuring an object, the apparatus including a projecting unit for projecting examination luminous flux for alignment, examination, and measurement to the object, a light delivery optical system for delivering the examination luminous flux to the object or a photodetector, an optical member for splitting or combining the examination luminous flux, the optical member being disposed obliquely in an optical path of the light delivery optical system, and the optical member including a base body made of a transparent material originally having an internal transmittance of approximately 100%, and the base body having a light entrance plane and a light exit plane and including a colored portion whereby an internal transmittance of the optical member is reduced.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

A detailed description of preferred embodiments of an optical member, an observation apparatus with the optical member, and an examination apparatus with the optical member embodying the present invention will now be given referring to the accompanying drawings.

Figure 1:
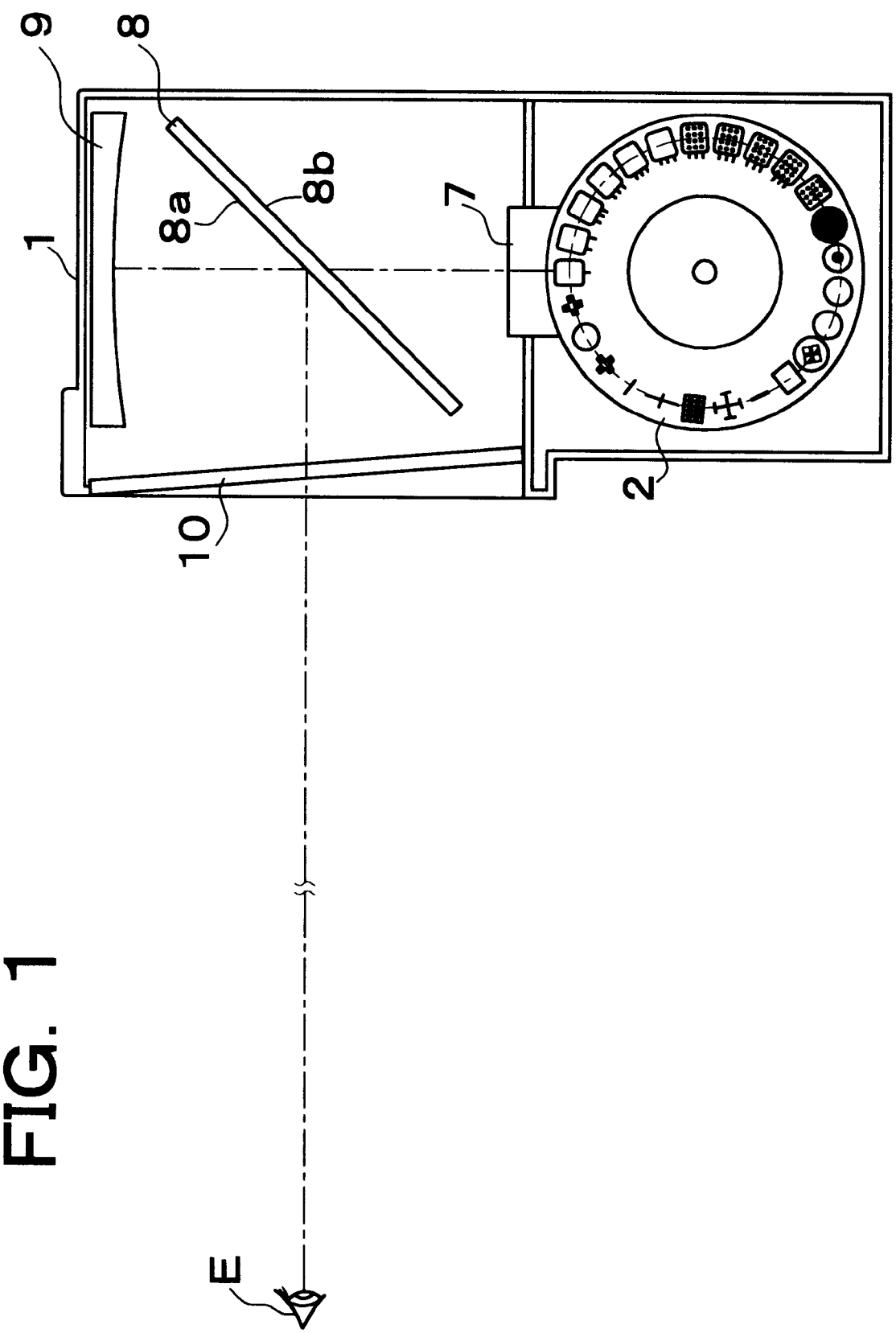
FIG. 1 is a schematic right side view of an optical system in a space-saving type visual function examination apparatus in a first preferred embodiment according to the present invention.
Figure 2:
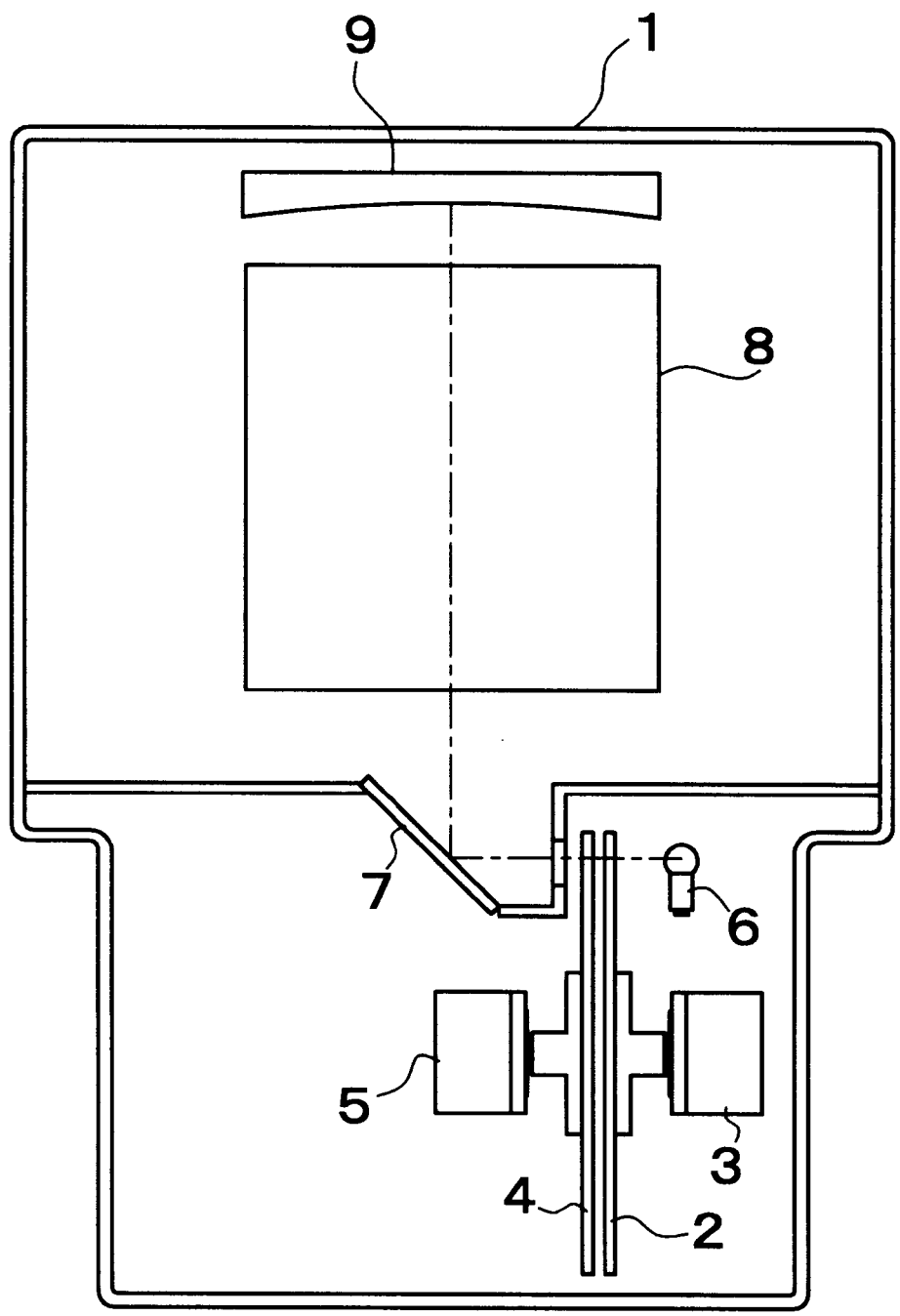
FIG. 2 is a schematic front view of the optical system in the apparatus of FIG. 1.

FIG. 1 is a schematic right side view of an optical system in a visual function examination apparatus of a space-saving type in a first embodiment according to the present invention. FIG. 2 is a schematic front view of the optical system in the apparatus of FIG. 1.

Reference alphabet E is an eye of an examinee. In a main body 1 of the visual function examination apparatus in the present embodiment, an optotype disc plate 2 made of glass, on which many optotypes, such as optotypes for vision test, are provided in a circle by means of chrome evaporation and the like. This optotype disc plate 2 is rotated by a motor 3 to change an optotype to be presented to the examinee. As shown in FIG. 2, a mask plate 4 for partially masking the optotypes is disposed facing to the optotype disc plate 2. This mask plate 4 is rotated by a motor 5 to cover the optotypes needed to be masked.

In the main body 1, also provided are an illumination lamp 6 for illuminating the disc plate 2 to project an optotype for examination, and a mirror 7 for reflecting the illumination light (i.e., optotype light) emitted from the lamp 6 upward in FIGS. 1 and 2. A beam splitter 8 formed like a flat plate is disposed above the mirror 7. This beam splitter 8 has a half mirror plane (i.e., a light exit side) 8a with a half mirror film applied thereon and a back plane (i.e., a light entrance side) 8b with an antireflective film applied thereon. The beam splitter 8 is constructed of a base body of which an entire interior is uniformly colored to absorb a part of visible light (namely, to reduce the internal transmittance to visible light). Coloring the interior of the base body is conducted by doping a dye in a producing process of a material configuring the base body. Alternatively, the base body may be colored on only its surface (at least one of the planes 8a and 8b). Coloring the surface of the base body is conducted by dispersing a dye and chrome-evaporating the dispersed dye to the surface. The base body of the beam splitter 8 is made of a material suitable for production of beam splitters, such as glass, acryl, and the like. As the color of the dye, gray, green, and the like are desirable in the present embodiment.

A concave mirror 9 is disposed above the beam splitter 8. In the present embodiment, this concave mirror 9 is so designed as to adjust an optical path length between the examination optotype and the examinee's eye E to an examination distance of 5 m when the distance between the examinee's eye E and the apparatus body 1 is 1.1 m.

In the visual function examination apparatus 1 having the above configuration, light emitted from the lamp 6 illuminates the optotype on the disc plate 2, and the light of the optotype is reflected by the mirror 7 toward a beam splitter 8. The luminous flux passed through the beam splitter 8 is reflected by the concave mirror 9 toward the beam splitter 8 again. A part of the luminous flux returned to the beam splitter 8 is reflected by the half mirror plane 8a and directed toward the examinee's eye E through a window 10. This allows the examinee's eye E to view the optotype optically placed at a predetermined examination distance. A visual function examination such as a vision test is thus effected.

As mentioned above, the regular luminous flux of the optotype (which is hereinafter referred to as a main light beam) is delivered to the examinee's eye E. In addition, in the configuration that the beam splitter 8 is obliquely disposed with respect to the optical path of the optical system, as will be mentioned in detail later, a part of the luminous flux of the optotype split from the main light beam by the half mirror plane 8a is reflected by the back plane 8b of the beam splitter 8, thereby forming an optical path of ghost luminous flux (which is hereinafter referred to as a satellite light beam).

Figure 3:
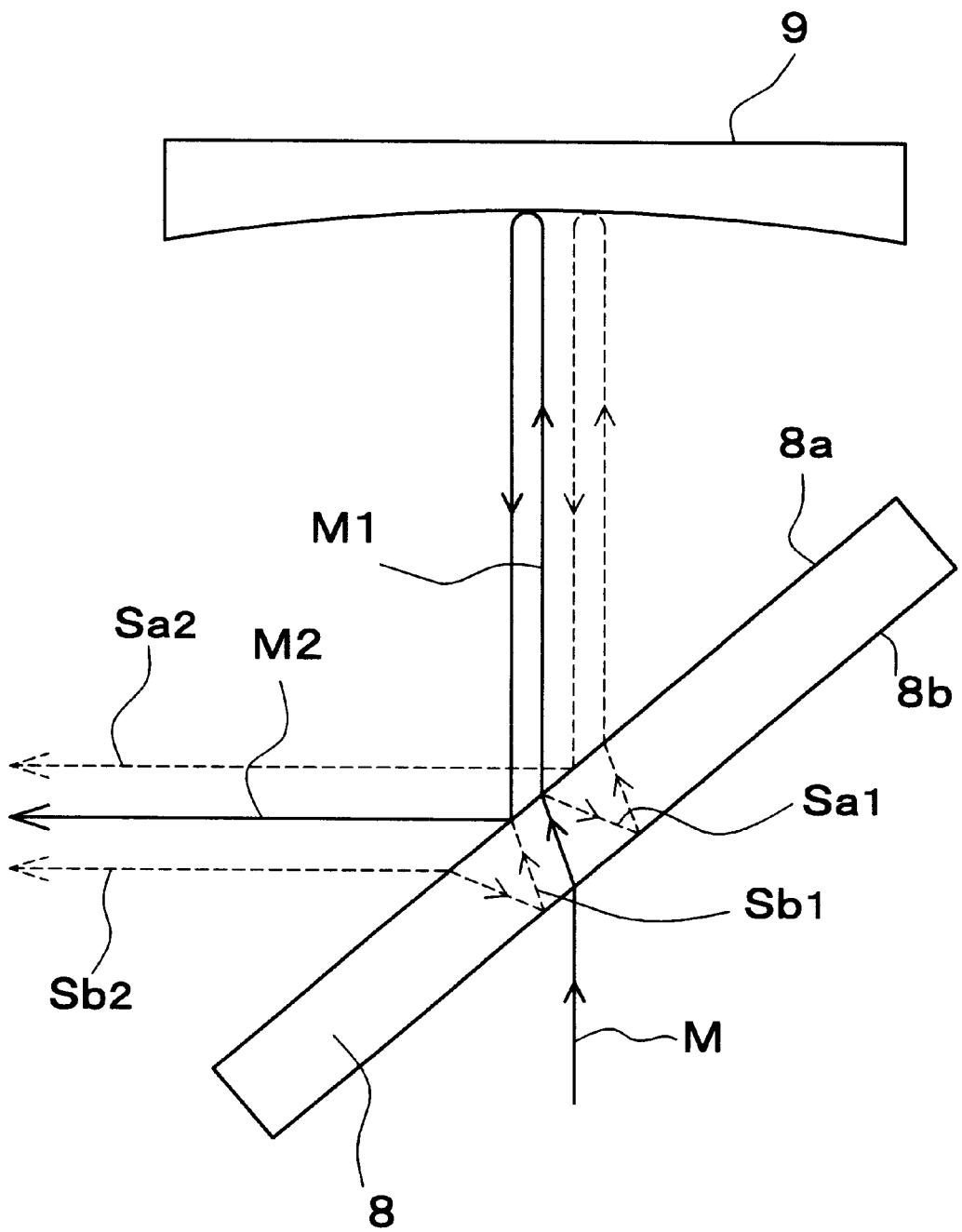
FIG. 3 is an explanatory view showing optical paths of light beams which are split or combined by a beam splitter in the apparatus of FIG. 1.

Specifically, as shown in FIG. 3 which is a schematic view of optical paths of the light beams, the optotype luminous flux M that has entered the beam splitter 8 is split into a main light beam M1 which travels through the inside of the beam splitter 8 and passes through the half mirror plane 8a and a first satellite light beam Sa1 which is reflected by the same plane 8a. The light beam Sa1 travels through the beam splitter 8 to the back plane 8a, as indicated by a dotted line in FIG. 3. Then, most of the light beam Sa1 passes through the back plane 8b due to an antireflective film applied thereon, while a part of the light beam Sa1 is reflected by the back plane 8b and travels through the beam splitter 8 again and a part of the reflected light beam passes through the half mirror plane 8a to the outside. Of the light beam Sa1, the light passed through the half mirror plane 8a is reflected by the concave mirror 9 to return to the half mirror plane 8a and reflected by this plane 8a to form a first satellite light beam Sa2 to be directed to the examinee's eye E.

On the other hand, the main light beam M1 that has passed through the half mirror 8a is reflected by the concave mirror 9 as mentioned above and is returned to the beam splitter 8, and is split into a main light beam M2 which is deflected by the half mirror plane 8a toward the examinee's eye E and a second satellite light beam Sb1 which passes through the half mirror plane 8a. The light beam Sb1 travels through the beam splitter 8 to the back plane 8b and is thereby reflected by the back plane 8b to travel through the beam splitter 8 again. At the time of passing through the half mirror plane 8a, the light beam is refracted to form a second satellite light beam Sb2 to be directed to the examinee's eye E.

Actually, after the above, light splitting by the half mirror plane 8a and light reflection by the back plane 8b are conducted plural times, which will produce satellite beams of a high order. However, the light amount of those light beams are as extremely low as it may be disregarded during observation of the optotype. This specification therefore makes no mention thereof.

Next, explanation is made on the reduction of the light amount of the satellite light beams produced as above, using the beam splitter 8 which is configured of a base body of which interior or surface is so colored as to have the property of absorbing a part of visible light.

The internal transmittance of the base body of the beam splitter 8 is regarded as "$\tau$", which varies with the coloring degree of the base body. The transmittance of the half mirror plane 8a is regarded as "T", and the reflectance of the same is regarded as "R". It is to be noted that, if a metal film is used as the half mirror film, it having a property of optical absorption, the transmittance T and the reflectance R are less than 1, namely, T+R<1. The reflectance of the back plane 8 applied with an antireflective film is regarded as "r" and the transmittance of the same is regarded as "1−r". In this case, a dielectric film is used as the antireflective film to enable substantial disregard of the optical absorption. The reflectance of the concave mirror 9 is regarded as "$R_0$".

In the case where the optical members have respective optical properties as above and the light amount of the optotype light beam M which enters the beam splitter 8 is regarded as 1, the light amount of each of the main light M2, the first satellite light Sa2, and the second satellite light Sb2, all of which are directed to the examinee's eye E, is determined as below.

<The light amount of the main light M2>

The light beam M passes through the antireflective film having the transmittance (1−r), the interior of the beam splitter 8 having the internal transmittance $\tau$, and the half mirror plane 8a having the transmittance T, so that the light amount of the light beam M1 becomes "T(1−r)$\tau$". This light beam is reflected by the concave mirror 9 having the reflectance $R_0$ and the half mirror plane 8a having the reflectance R in turn. The light amount IM of the resultant light beam M2 is expressed by the following formula (1);

$$IM = TR(1-r)\tau R_0 \tag{1}$$

<The light amount of the first satellite light Sa2>

The light beam Sa2 results from the light beam Sa1 reflected by the half mirror plane 8a and the back plane 8b of the beam splitter 8, so that the light beam Sa2 travels through beam splitter 8 more than the light beam M2 by two times and, furthermore, it is reflected by the half mirror plane 8a with the reflectance R and the antireflective film with the reflectance r. Accordingly, the light amount "Ia" of the resultant light beam Sa2 is expressed by the following formula (2);

$$Ia = TR^2 r(1-r)\tau^3 R_0 \tag{2}$$

<The light amount of the second satellite light Sb2>

The light beam Sb2 results from the light beam Sb1 split from the main light beam M1 reflected by the concave mirror 9, so that the light beam Sb2 has passed twice through the half mirror plane 8a with the transmittance T and traveled twice through the beam splitter 8, and been reflected once by the back plane 8b with the reflectance r. Accordingly, the light amount "Ib" of the resultant light beam Sb2 is expressed by the following formula (3);

$$Ib = T^3 r(1-r)\tau^3 R_0 \tag{3}$$

As mentioned above, the light beam M2 travels only once through the beam splitter 8, while the light beams Sa2 and Sb2 travel three times through the same. It is therefore understood that the light beams Sa2 and Sb2 receive the influence of the internal transmittance $\tau$ more than the light beam M2 does.

Regarding the light amount ratio of the light beams Sa2, Sb2 to the light beam M2 as Pa, Pb, respectively, these ratios Pa and Pb are expressed by the following formulas (4) and (5);

$$Pa = Ia/IM = Rr \times \tau^2 \tag{4}$$

$$Pb = Ib/IM = (T^2 r/R) \times \tau^2 \tag{5}$$

As these values Pa, Pb which are the ratios of the satellite light beams to the light beam M2 decrease, the satellite light beams are hard to be conspicuous. In order to decrease the values Pa, Pb at the same time without changing the reflectance R and the transmittance T of the half mirror plane 8a in consideration of a limitation on a spec constraint on apparatus, accordingly, it is sufficient to reduce the internal transmittance $\tau$ of the beam splitter 8 and the reflectance r of the antireflective film. However, there is a limitation to reduce the reflectance r of the antireflective film. On the other hand, the values Pa, Pb are proportional to the square of the internal transmittance $\tau$, and the amount of the ghost light which should form ghost images can be efficiently and easily reduced if $\tau$ is lowered.

Next, the reducing effect of the amount of satellite light beams (ghost images) is explained by substituting concrete numerical values in the above formulas representing the properties of the optical members, thereby changing the internal transmittance $\tau$ of the beam splitter 8.

At first, 45% is substituted for the transmittance T of the half mirror film applied onto the beam splitter 8; 45%, for the reflectance R of the same; 0.5%, for the reflectance r of the antireflective film applied to the back plane 8b (i.e., the transmittance thereof is 99.5%); and 95%, for the reflectance $R_0$ of the concave mirror 9. Under this condition, in each case of the internal transmittance $\tau$ of 99.9% (which is the case where the base body configuring the beam splitter 8 is made of a transparent material such as glass as in conventional cases), 90%, and 80%, the light amount ratios Pa, Pb are obtained by means of the formulas (4) and (5). It is to be noted that the resultant number is round off to the sixth decimal place.

In the case of τ=99.9%, Pa=0.00225 and Pb=0.00225.

In the case of τ=90%, Pa=0.00182 and Pb=0.00182. The ratio of this case to the case of τ=99.9% is 0.00182/0.00225= approximately 0.808. This means that about 20% reduction of the light amount of the satellite light beam can be effected, while retaining the light amount of the main light beam M2 as same as in the case of τ=99.9% (by increasing the light amount of the light source so that the light amount of the main light beam M2 equals to that in the case of τ=99.9%).

In the case of τ=80%, Pa=0.00144 and Pb=0.00144. The ratio of this case to the case of τ=99.9% is 0.00144/0.00225= 0.64. This means that about 36% reduction of the light amount of the satellite light beam can be effected, while retaining the light amount of the main light beam M2 as same as in the case of τ=99.9% (by increasing the light amount of the light source so that the light amount of the main light beam M2 equals to that in the case of τ=99.9%).

It is to be noted that lowering the transmittance τ also causes the reduction of the light amount of the main light beam itself to be directed to the examinee's eye E. However, by adjusting the light amount of the lamp 6 and the transmittance τ, the light amount of the superfluous satellite light beam can be reduced, while the necessary light amount of the main light beam can be ensured. If the transmittance to be determined is higher than 90%, the reduction of the satellite light beam can not be achieved to a desired extent, which is impractical. To the contrary, if the transmittance is less than 70%, which causes a shortage of the light amount of the main light beam, the light source is required adjusting to produce a large amount of light. Accordingly, the transmittance τ is preferably determined in a range of 70–90%.

In the first embodiment, as mentioned above, the light amount of the main light beam can be kept to the extent needed for observation or examination with respect to an object (an examinee's eye E), while the light amount of the ghost light which is generated in association with the main light can be reduced, thereby enabling efficient observation or examination.

In the above embodiment, the beam splitter having the property of splitting luminous flux by transmitting or reflecting the luminous flux at a predetermined ratio is exemplified. Instead thereof, the beam splitter having the property of splitting luminous flux by transmitting or reflecting the luminous flux according to wavelengths may be used.

In the above first embodiment, the beam splitter is used as an optical member for transmitting or reflecting luminous flux while efficiently reducing satellite light. The present invention is not limited thereto. For an alternative of the optical member, a beam combiner which combines a plurality of light beams may be used.

Figure 4:
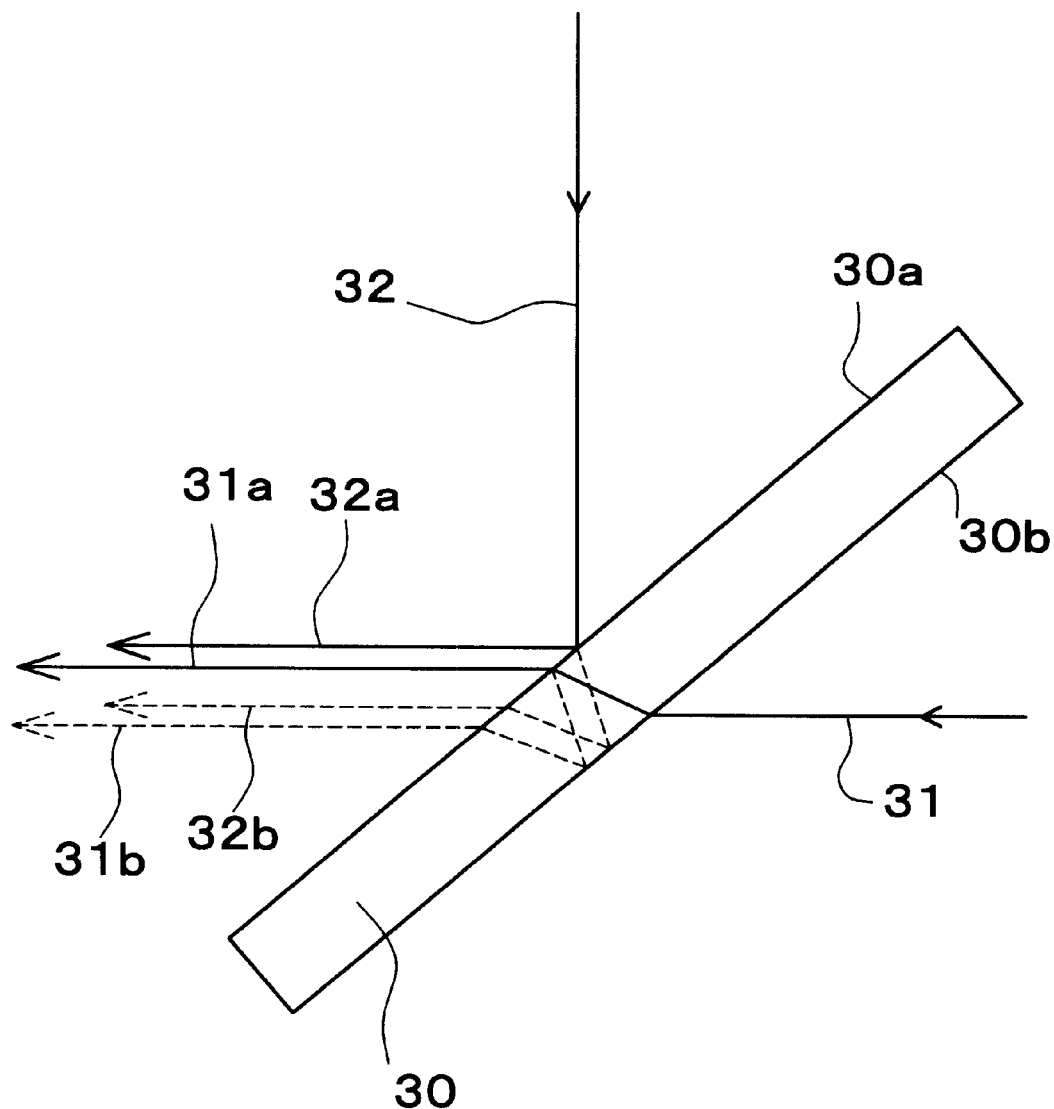
FIG. 4 is an explanatory view showing optical paths of light beams which are split or combined by a beam combiner used as an alternative of an optical member in the first embodiment.

FIG. 4 shows a dichroic mirror as an example of the beam combiner. This dichroic mirror 30 is applied with a mirror film on a plane 30a. The mirror film has the property of allowing a light beam 31 having a first wavelength (e.g., visible light) which comes from the right in FIG. 4 to pass, while reflecting a light beam 32 having a second wavelength (e.g., near-infrared light) which comes from above in FIG. 4. Generally, the mirror film even if configured as above does not completely transmit or reflect the light beams, and a part of the light beams that has not been transmitted or reflected remains in the dichroic mirror 30. The remaining light beams are reflected by the plane 30b to form ghost light beams 31b, 32b as illustrated by dotted lines in FIG. 4 with respect to main light beams 31a, 32a which are combined to each other. The ghost light beam 31b travels three times through the inside of the dichroic mirror 30, namely, two times more than the main light beam 31a does. The ghost light beam 32b travels twice through the same, namely, two times more than the main light beam 32a does. Accordingly, a base body of the dichroic mirror 30 is so colored, in a similar coloring manner in the first embodiment, as to absorb the light beams having the first and second wavelengths in order to reduce the internal transmittance of the base body. In this way, the dichroic mirror 30 of which the base body is colored according to the wavelengths of light beams to transmit or reflect can prevent the generation of ghost light beams.

Although the visual function examination apparatus is exemplified in the above embodiment, the present invention can be applied to various apparatus desired to prevent the influence of ghost light, for example, an observation apparatus for observing or imaging (photographing) an object by means of light reflected by or transmitted through the object illuminated by an illumination lamp and the like, an examination apparatus for examining or measuring an object by projecting a light beam for alignment, examination, or measurement to the object, and also apparatus besides ophthalmic apparatus.

Figure 5:
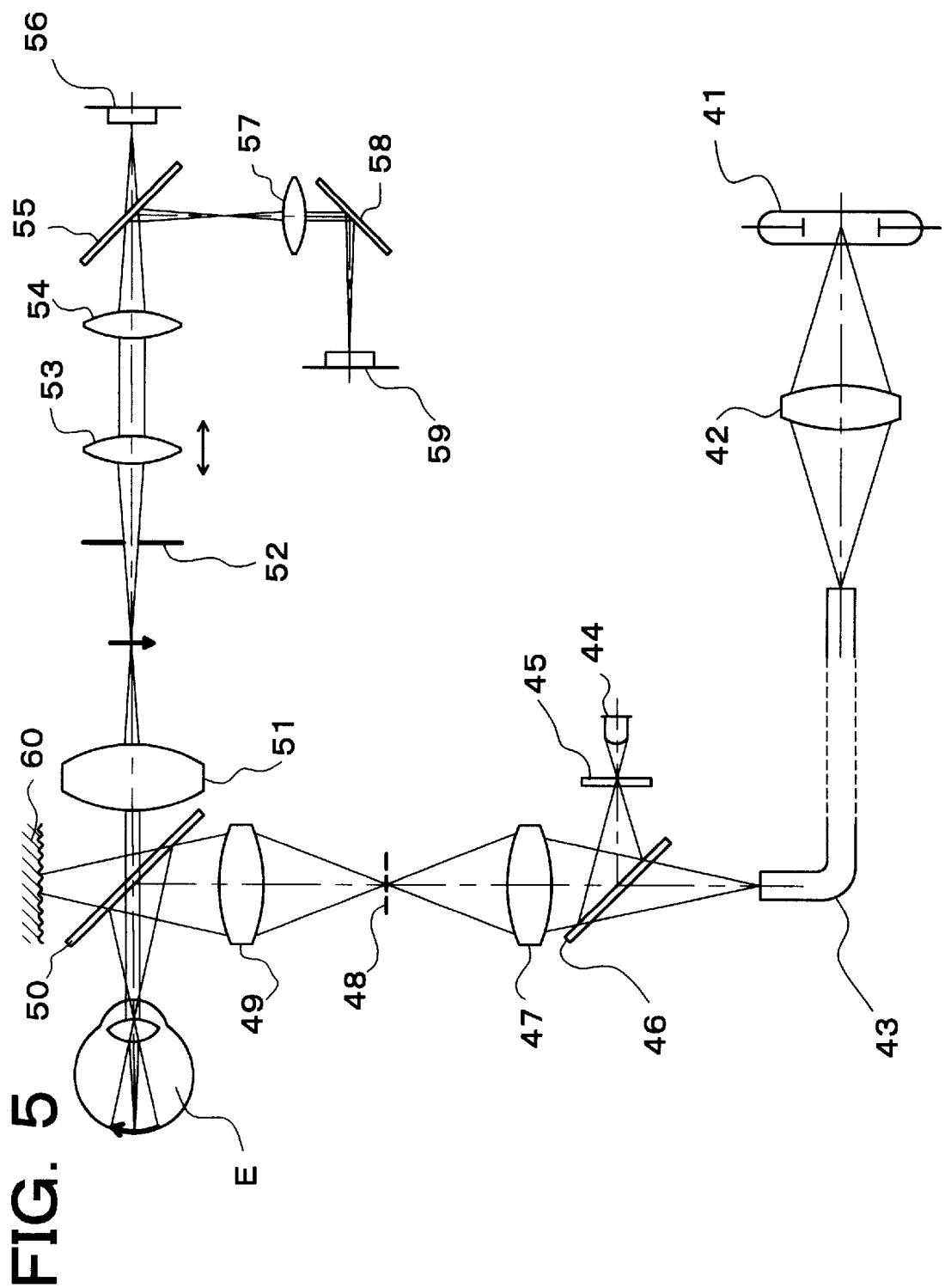
FIG. 5 is a schematic structural view of an optical system of a fundus camera which images (photographs) the fundus of an examinee's eye in a second preferred embodiment according to the present invention.

Next, explanation is made on a second preferred embodiment according to the present invention applied to an observation apparatus provided with such optical members as mentioned in the first embodiment. The observation apparatus is embodied in a fundus camera which images (photographs) the fundus of an examinee's eye. FIG. 5 is a schematic structural view of an optical system of the fundus camera. In this optical system, a visible light beam emitted from a flash lamp 41 for imaging is condensed by a condenser lens 42 to enter a fiber 43. Numeral 46 denotes a beam combiner having the property of reflecting infrared light, while transmitting visible light. The imaging light beam exits from the fiber 43 and is combined by the beam combiner 46 with an infrared light beam for observation which is emitted from an illumination light source 44 for observation and then diffused by a diffusing plate 45. The combined light beam of the imaging light and the observing light passes through a condenser lens 47 and a slit plate 48 having a center portion which blocks light and a ring-like slit surrounding the center portion.

Then, the observing light and the imaging light passes through a light projecting lens 49 and is reflected by a beam splitter 50 toward the examinee's eye E. This beam splitter 50 has the property of reflecting a part of the imaging and observing light beams toward the examinee's eye E, while transmitting a part of the imaging and observing light beams reflected by the fundus of the eye E. The light beam reflected by the fundus of the eye E is transmitted through the beam splitter 50, and then an objective lens 51, an imaging diaphragm 52 disposed in a position conjugated with the pupil of the eye E, a focusing lens 53 which is movable along an optical axis, and an image forming lens 54, and enters the beam splitter 55. This beam splitter 55 has the property of reflecting infrared light, while transmitting visible light, thereby to split the light which enters the beam splitter 55 into an infrared light beam and a visible light beam. The observing light beam which is infrared light is reflected by the beam splitter 55 toward a relay lens 57 and a mirror 58, and deflected by the mirror 58 toward an observing CCD camera 59. On the other hand, the imaging light beam which is visible light passes through the beam splitter 55 and falls on an imaging CCD camera 56.

Numeral 60 denotes a black absorption member for absorbing a light beam that passed through the beam splitter 50 for the purpose of preventing unnecessary noise light from entering the cameras 56, 59.

In the observation apparatus provided with the optical system mentioned above, the beam splitters 50 and 55 are configured, like the beam splitter 8 in the first embodiment, with the base body of which the entire interior or only the surface is colored. Accordingly, the thus configured optical members can reduce the generation of ghost images when the reflection light from the fundus of the examinee's eye E illuminated by the imaging light emitted from the imaging light source 41 and the illumination light emitted from the illumination light source 44 is observed and imaged (photographed) through the above optical system. With the observation apparatus configured as above, the fundus image of the examinee's eye E can be efficiently observed or imaged with no influence of ghost images.

Figure 6:
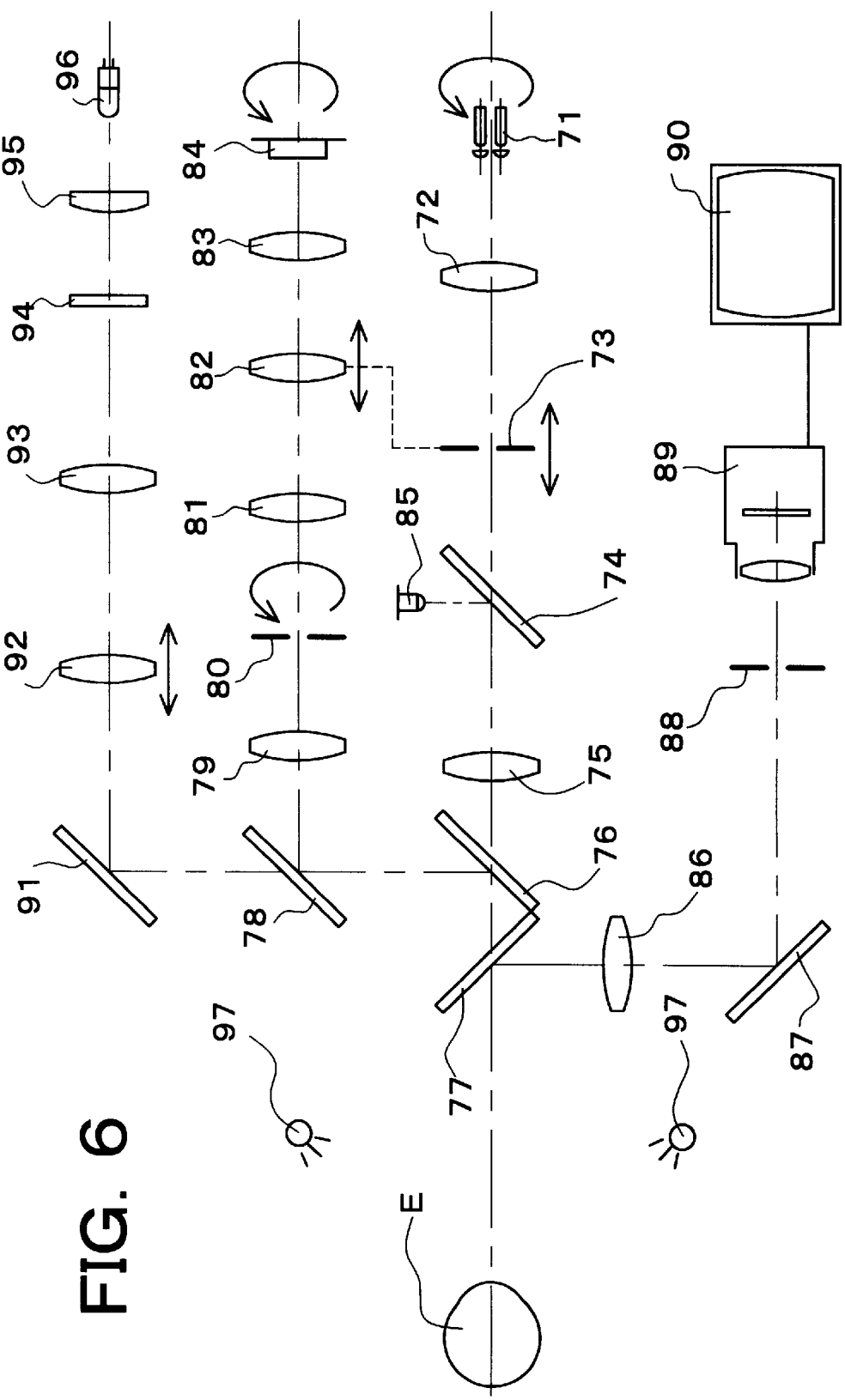
FIG. 6 is a schematic structural view of an optical system of an eye refractive power measurement apparatus which measures the refractive power of an examinee's eye in a third preferred embodiment according to the present invention.

Furthermore, explanation is made on a third preferred embodiment according to the present invention applied to an eye-refractive power measurement apparatus which measures the refractive power of an examinee's eye, provided with such optical members as mentioned in the first embodiment. FIG. 6 is a schematic structural view of an optical system of the measurement apparatus in the third embodiment. This optical system mainly includes a first light delivery optical system for delivering light beams for measurement and for illumination to an examinee's eye E and a second light delivery optical system for delivering light beams reflected by the eye E to a photodetector and an observing and imaging (photographing) unit, individually.

In the first light delivery optical system which delivers the measuring light beams to the eye E, an infrared light beam emitted from two measuring light sources 71 is condensed by a condenser lens 72 and passes through a target plate 73 which is movably along the optical axis and disposed in a position conjugated with the fundus of the eye E. Numeral 74 denotes a beam combiner having the property of transmitting infrared light for measurement, while reflecting infrared light for alignment which will be mentioned later, thereby to combine them. The measurement light beam that passed through the target plate 73 is combined by the beam combiner 74 with a light beam emitted from a spot light source 85 which emits the light beam for alignment having an infrared wavelength different from the measurement light. The combined light beams are projected to the eye E through a projection lens 75, beam splitters 76 and 77 disposed on the optical axis of the first light delivery optical system.

The beam splitter 76 has the property of transmitting and reflecting infrared light, while reflecting visible light. The beam splitter 77 has the property of transmitting and reflecting infrared light, while transmitting visible light. A beam splitter 78 is disposed on the optical axis of a reflection light from the beam splitter 76. This beam splitter 78 has the property of transmitting visible light, while reflecting infrared light.

The light for measurement reflected by the fundus of the eye E passes through the beam splitter 77 and is reflected by the beam splitters 76 and 78 in turn to pass through relay lenses 79 and 81. Numeral 80 is a mask for blocking the light reflected from the cornea of the eye E, disposed in a position conjugated with the cornea of the eye E. The light beam that passed through the relay lens 81 then passes through a lens 82 which is movable along the optical axis in synchronization with the target plate 73, and an image forming lens 83, and falls on a measuring-light receiving element 84 serving as a photodetector. This light receiving element 84 is rotated about the optical axis in synchronization with the light source 71 and the mask 80.

On the other hand, a part (alignment light) of the reflected light beams from the eye E is reflected by the beam splitter 77 toward the objective lens 86, transmitted therethrough, and reflected by a mirror 87, and finally falls on a CCD camera 89 through a telecentric diaphragm 88. The images of the eye E and the alignment light imaged with the CCD camera 89 are projected on an observing monitor 90 to allow an operator to conduct alignment between the eye E to be examined and the apparatus.

Furthermore, the visible illumination light beam emitted from an illumination lamp 96 passes through a condensing lens 95, a first fixation target 94, and a first and second relay lenses 92, 93. The light beam is then deflected by a mirror 91 and by the beam splitter 76 toward the eye E to project an image of the first fixation target 94 on the eye E. Numeral 97 denotes an illumination light source which emits illumination light having substantially the same wavelength as the alignment light to illuminate the anterior part of the eye E.

In the above apparatus, the beam splitters 76, 77, 78 and the beam combiner 74 are, like the beam splitter 8 in the first embodiment, configured of the base body of which the entire interior or only at least one surface of a light entrance plane and a light exit plane is colored. Accordingly, the thus configured optical members can reduce the generation of ghost light, so that the eye-refractive power of the eye E can be properly measured.

As described in detail in the above preferred embodiments, the optical member such as the beam splitters 8, 50, 55, 76–78, and the beam combiners 30, 74 is constructed of the base body of which the entire interior or only at least one plane is so colored as to absorb a part of visible light or infrared light (thereby to reduce the internal transmittance to visible light. This makes it possible to reduce the amount of ghost light while ensuring the amount of light needed for observation or examination of an object (i.e., an examinee's eye E in the above embodiments), thus preventing the influence of ghost images. Accordingly, the observation or examination apparatus provided with the above optical members enables efficient observation or examination of the object.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An optical member for splitting or combining luminous flux, the optical member including:
   a base body made of a transparent material originally having an internal transmittance of approximately 100%, the base body having a light entrance plane and a light exit plane and including a colored portion whereby an internal transmittance of the optical member is reduced.

2. The optical member according to claim 1, wherein the colored portion is formed in an entire interior of the base body.

3. The optical member according to claim 1, wherein the colored portion is formed on at least one of the light entrance plane and the light exit plane.

4. The optical member according to claim 1, wherein the colored portion of the base body is so colored as to have the internal transmittance determined in a range of 70 to 90%.

5. The optical member according to claim 2, wherein the colored portion is formed in the entire interior of the base body by doping a dye in the transparent material configuring the base body.

6. The optical member according to claim 3, wherein the colored portion is formed on at least one of the light entrance plane and the light exit plane by diffusing and vapor-depositing a dye onto the base body configured of the transparent material.

7. The optical member according to claim 1 including a beam splitter for splitting the luminous flux which enters the beam splitter by reflecting a part of the luminous flux and transmitting another part of the luminous flux at a predetermined ratio with respect to a light amount.

8. The optical member according to claim 1 including a beam splitter for splitting the luminous flux which enters the beam splitter by reflecting a part of the luminous flux and transmitting another of the luminous flux according to wavelengths.

9. The optical member according to claim 1 including a beam combiner for combining luminous flux which enters the beam combiner from different two directions by transmitting the luminous flux of a first wavelength and reflecting the luminous flux of a second wavelength which is different from the first wavelength.

10. An observation apparatus for observing or imaging an object by means of observation luminous flux which is a light reflected from or transmitted through the object illuminated, the apparatus including:

an illumination light source for emitting an illumination light to illuminate the object;

a light delivery optical system for delivering the observation luminous flux from the object illuminated by the illumination light source to an eye of an observer and an imaging unit; and an optical member for splitting or combining the observation luminous flux, the optical member being disposed obliquely in an optical path of the light delivery optical system, and the optical member including a base body made of a transparent material originally having an internal transmittance of approximately 100%, and the base body having a light entrance plane and a light exit plane and including a colored portion whereby an internal transmittance of the optical member is reduced.

11. The observation apparatus according to claim 10, wherein the colored portion is formed in an entire interior of the base body.

12. The observation apparatus according to claim 10, wherein the colored portion is formed on at least one of the light entrance plane and the light exit plane.

13. The observation apparatus according to claim 10, wherein the colored portion of the base body is so colored as to have the internal transmittance determined in a range of 70 to 90%.

14. The observation apparatus according to claim 10, including an ophthalmic observation apparatus for observing or imaging an eye to be examined by the observation luminous flux which is the light reflected from or transmitted through the eye illuminated by the illumination light.

15. An examination apparatus for examining or measuring an object, the apparatus including:

a projecting unit for projecting examination luminous flux for alignment, examination, or measurement to the object, a light delivery optical system for delivering the examination luminous flux to the object or a photodetector;

an optical member for splitting or combining the examination luminous flux, the optical member being disposed obliquely in an optical path of the light delivery optical system, and the optical member including a base body made of a transparent material originally having an internal transmittance of approximately 100%, and the base body having a light entrance plane and a light exit plane and including a colored portion whereby an internal transmittance of the optical member is reduced.

16. The examination apparatus according to claim 15, wherein the colored portion is formed in an entire interior of the base body.

17. The examination apparatus according to claim 15, wherein the colored portion is formed on at least one of the light entrance plane and the light exit plane.

18. The examination apparatus according to claim 15, wherein the colored portion of the base body is so colored as to have the internal transmittance determined in a range of 70 to 90%.

19. The examination apparatus according to claim 15, including an ophthalmic examination apparatus for examining or measuring an eye to be examined by projecting the examination luminous flux for alignment, examination, or measurement to the eye.

20. The examination apparatus according to claim 19, wherein the projecting unit including an optotype plate provided with examination optotypes to be presented to the eye to be examined, and an illumination unit for illuminating the examination optotype to be presented, and the light delivery optical system delivers luminous flux of the optotype of the optotype plate illuminated by the illumination unit to present the examination optotype to the eye to be examined.

21. The examination apparatus according to claim 20 further including a concave mirror for reflecting the optotype luminous flux passed through the optical member, wherein the optical member deflects the optotype luminous flux after reflected by the concave mirror toward the eye to be examined.

* * * * *